United States Patent [19]

Ramsey et al.

[11] Patent Number: 4,705,948

[45] Date of Patent: Nov. 10, 1987

[54] CLOSED-LOOP PULSED HELIUM IONIZATION DETECTOR

[75] Inventors: Roswitha S. Ramsey; Richard A. Todd, both of Knoxville, Tenn.

[73] Assignee: The United States of America as represented by the United States Department of Energy, Washington, D.C.

[21] Appl. No.: 831,942

[22] Filed: Feb. 24, 1986

[51] Int. Cl.[4] ............................................. H01J 47/02
[52] U.S. Cl. ..................................... 250/386; 250/379
[58] Field of Search ............... 250/386, 382, 384, 381, 250/374, 379; 324/465, 464

[56] References Cited

U.S. PATENT DOCUMENTS

| | | | |
|---|---|---|---|
| 3,634,754 | 1/1972 | Lovelock et al. | 324/33 |
| 3,897,344 | 7/1975 | Marshall, III et al. | 250/386 |
| 4,117,332 | 9/1978 | Felton et al. | 250/374 |
| 4,538,066 | 8/1985 | Carle et al. | 250/374 |

OTHER PUBLICATIONS

Andrawes et al, "Saturation Region of HID . . . ", Anal. Chem. 52 (1980), 891.
Lovelock, J., "EAD and Technique for use . . . ", Anal. Chem. 35 (1963), 474.

Primary Examiner—Carolyn E. Fields
Assistant Examiner—Richard Hanig
Attorney, Agent, or Firm—David E. Breeden; Stephen D. Hamel; Judson R. Hightower

[57] ABSTRACT

A helium ionization detector for gas chromatography is operated in a constant current, pulse-modulated mode by configuring the detector, electrometer and a high voltage pulser in a closed-loop control system. The detector current is maintained at a fixed level by varying the frequency of fixed-width, high-voltage bias pulses applied to the detector. An output signal proportional to the pulse frequency is produced which is indicative of the charge collected for a detected species.

6 Claims, 6 Drawing Figures

CLOSED-LOOP PULSED HELIUM IONIZATION DETECTOR

This invention is a result of a contract with the U.S. Department of Energy.

BACKGROUND OF THE INVENTION

This invention relates generally to the art of helium ionization detectors and more specifically to improvements in helium ionization detection systems.

The helium ionization detector (HID) is one of the most sensitive detectors currently available for gas chromatography. The detector is nonselective, meaning that it is capable of responding to all chromatographable species ranging from the permanent gases to complex organic molecules. Despite its universal response mechanism and high ionization efficiency, the HID detector has not been widely used. The reasons for its limited use include the stringent requirements for high sensitivity operation, instability, and variations in response for selected species as a function of chromatographic conditions. The greatest sensitivity is obtained when ultrapure helium is used as the carrier gas and when contributions from the chromatographic system (e.g., column bleed) to the background current are minimal. Low parts-per-billion concentrations of the permanent gases can be determined under these conditions.

The universal response characteristic which is largely an advantage can also be troublesome since any atmospheric diffusion into the system will reduce the sensitivity of the detector. Long periods of time may be required to stabilize the detector on initial start-up, when changing separation columns, or following any exposure of the system to the atmosphere. The response to the substrate or solvent may also be excessively large requiring long periods between sample analyses to allow the detector to return to initial background conditions. When the detector is over loaded by high concentrations of an analyte, or if the background is high, anomalous peak shapes or polarity inversions may be obtained making it difficult to interpret the results.

Despite these problems, there has been renewed interest in the HID. The characteristic negative response for the permanent gases has been examined and conditions which invert the signals defined. It has also been determined that the detector may be operated in the saturation region of the field intensity with sensitivities comparable to those which may be obtained in the exponential region (i.e., at greater than 350 V). This is due to a decrease in noise level and background current. These reductions, in turn, have allowed gas-liquid partition columns to be used with the detector which extends the applications to include higher molecular weight organics.

Conventionally, the HID has been operated only in a dc mode, wherein a constant polarizing voltage is applied across the cell and the ionization current is measured continuously. In this mode the detector is prone to spontaneous breakdown when high concentrations of an analyte are introduced into the cell. Further, the useful detecting range is rather narrow.

The performance of an HID has been recently improved by operating the detector in a pulsed mode in which the bias voltage applied to the detector is pulsed at a selected frequency and duty cycle to reduce noise and background current levels in the detector's output current response as compared to conventional dc bias operation. This technique is the subject of U.S. patent application for a "Pulsed Helium Ionization Detection System" by Ramsey et al, filed Apr. 9, 1985, presently identified as Ser. No. 721,339 and having a common assignee with the present invention, the subject matter of which is incorporated herein by reference thereto.

However, there is a need for further improvements to extend the analytical capabilities of an HID by extending the upper detection limits while reducing instability and maintaining its inherent sensitivity.

SUMMARY OF THE INVENTION

In view of the above need it is an object of this invention to provide an improved pulsed helium ionization detection system including feedback control of the detector pulsed operation which prevents spontaneous breakdown when high concentrations are introduced into the detector and increases dynamic range.

Other objects and many of the attendant advantages of the present invention will be apparent to those skilled in the art from the following detailed description of a preferred embodiment of the invention taken in conjunction with the drawings.

In summary, a conventional helium ionization detector is combined with a feedback control loop which pulses the detector bias voltage at a frequency to maintain a selected constant current through the detector as the analyte concentration varies. The control loop includes a stable, low-noise current source which injects a selected, fixed reference current into the input summing node of a low-noise, high-speed electrometer along with the ionization current signal from the detector. The output of the electrometer is amplified by low-noise gain stages and applied to the input of a voltage-to-frequency converter whose output controls the pulse rate of a high-voltage pulser. The voltage pulses from the pulser are applied to the detector and the frequency is varied by the control loop to maintain an average detector current equal to the fixed reference current.

Since the detector exhibits a low background current with high purity helium as the carrier gas, the highest frequency of operation is obtained at the lowest concentration of an analyte and decreases as the analyte concentration increases thereby preventing breakdown of the detector and extending the dynamic operating range. The closed-loop system increases the upper detection limit approximately 50 times over the conventional dc mode of operation.

DETAILED DESCRIPTION OF THE PREFERRED EMBODIMENT

Figure 1:
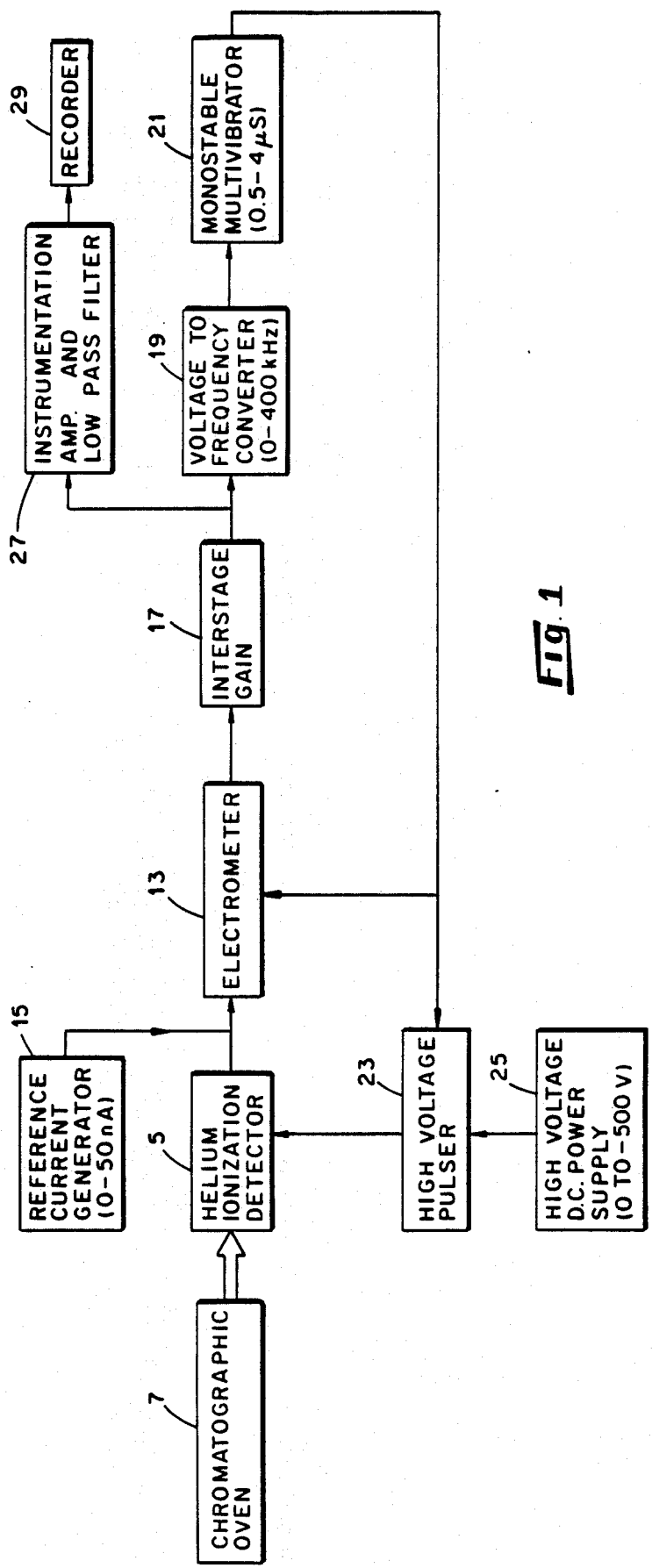
FIG. 1 is a schematic block diagram of a closed-loop helium ionization detection system according to the present invention.
Figure 2:
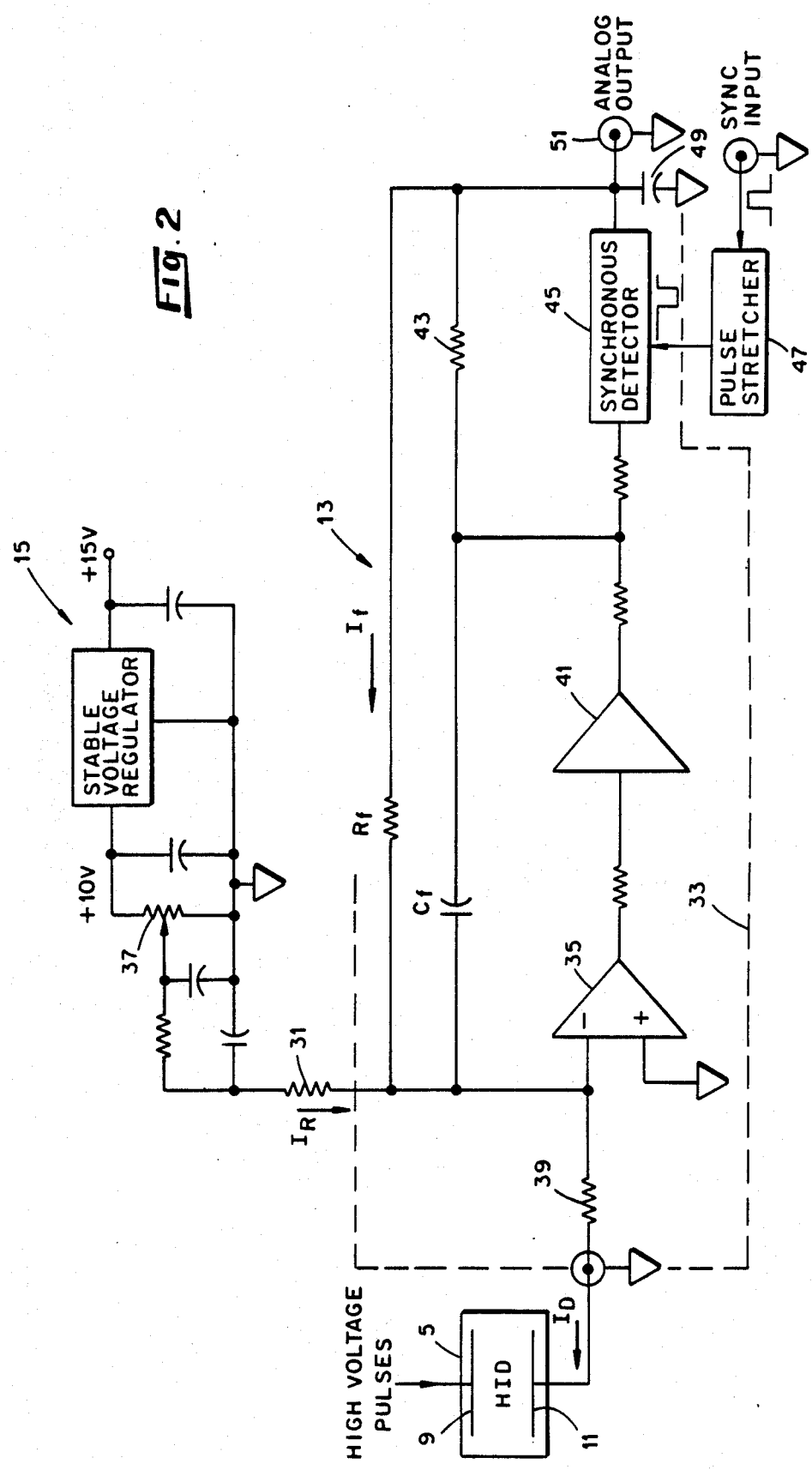
FIG. 2 is a schematic circuit diagram of the reference current circuit 15 and electrometer 13 shown in block form in FIG. 1.

Referring to FIG. 1, a conventional helium ionization detector (HID) 5, such as the Valco Model 100H available from Valco Instruments Co., Inc. Houston, Tex., is operated in a pulsed mode to detect components of a gas sample introduced into the detector from a separating column operated within a chromatographic oven 7. Details of this type of sampling system and the HID may be had by referring to the above-referenced application. The detector 5 includes a cathode 9 and an anode 11, as shown in FIG. 2, between which the gas flows. The anode is formed of a foil containing a radioactive source, such as 1Ci scandium tritide, which serves to ionize the sample gas components in the detector volume to produce an ionization current.

The anode of the detector 5 is connected to a summing junction input of an electrometer 13 together with a selected reference current from a stable reference current source 15 whose output may be varied over a range of from 0–50 nanoamperes. The output of the electrometer is fed through appropriate gain control circuitry 17 to the input of a voltage-to-frequency converter 19. The converter 19 produces an output pulse train having a frequency proportional to its input signal voltage. This pulse train is applied to the input of a variable period (0.5–4 microseconds) monostable multivibrator 21 which is triggered once each cycle of the input pulse train to produce switching pulses of selected and stable duration. At the highest operating frequency, the duty cycle is preferably 80% or greater which has been determined experimentally to produce the highest sensitivity. This pulse is applied to a high voltage pulser 23 which in turn applies high voltage bias pulses across the detector anode and cathode through switching of a bias voltage from a high voltage power supply 25. The bias voltage is applied to the detector for the duration of the switching pulse from the multivibrator 21. The multivibrator 21 period is adjusted to obtain the desired duty cycle of the high voltage pulse train applied to the detector under background conditions.

The high voltage pulser 23 is capable of operating from 0 to 500 volts from dc to greater than 300 kHz at the highest voltage. Thus, a variable voltage dc source 25 is used to allow the operator to adjust the bias voltage applied to the HID 5 in accordance with the particular application. One power supply which may be used is a Kepco Model APH 500M, Flushing, N.Y.

The chromatographic signal is extracted from the input to the voltage-to-frequency converter 19 and fed through an instrumentation amplifier and low pass filter network 27 to a recording device 29, such as a strip chart recorder, as will be more fully described herein below. This chromatographic signal is proportional to the change in frequency at which the detector is being pulsed and proportional to the concentration of the analyte being detected by the HID 5. The concentration of the analyte being detected is more closely proportional to the time difference between the inverse frequency and background period which can be easily determined by monitoring the output pulse frequency with a microprocessor based data acquisition sytem.

Referring now to FIG. 2, a schematic diagram of the reference current generator and the high speed electrometer circuit together with the HID 5 are shown. The reference current generator 15 shown at the top of the drawing, generates an adjustable reference current ($I_R$), typically set for 10 nA, which is selected in accordance with the desired operating current ($I_D$) level for the HID 5. The reference current ($I_R$) is generated by connecting a high megohm (200 meg) resistor 31 between the adjustable output of a stable reference voltage source through a grounded shield 33 to the inverting input (−) of a high speed amplifier 35, such as a model HA-5180 supplied by manufacture Harris Corporation, Orlando, Fla. which forms the input stage of the electrometer 13. A potentiometer 37 is provided at the output of a stable voltage regulator 15 to provide adjustment of the reference current $I_R$. The average detector current ($I_D$) is sensed by connecting the anode 11 of the detector 5 through a summing resistor 39 to the inverting input of amplifier 35. The noninverting input of amplifier 35 is connected to ground potential. The output of amplifier 35 is connected to the input of a buffer amplifier 41 whose output is connected to the inverting input of amplifier 35 through a 2000 pf capacitor $C_f$ and a resistor network including a resistor 43 and a resistor $R_f$, $R_f$ being a 400 megohm resistor, such that the feedback current ($I_f$) flowing through resistor $R_f$ is defined as follows:

$$I_f = I_D - I_r.$$

In order to detect only the dc component of the detector current a synchronous detector 45 is coupled to the output of the buffer amplifier 41 and is controlled by a sync signal from a pulse stretcher 47. The synchronous detector acts as a switch which is closed during the "off" period of the pulse from the monostable multivibrator (MV) 21, see FIG. 1. The pulse stretcher may take the form of a monostable multivibrator which is triggered "on" at the leading edge of each pulse from MV21 and has a period longer than the period of the MV21 pulse period so that when it times out a delayed low going signal (delayed approximately 200 n sec.) is applied to the detector, or switch 45, switching it "on" for the remaining low period of the MV21 pulse. This synchronous detection of the dc component of detector current decreases the high frequency ripple being introduced into the analog output signal from the electrometer 13 caused by the switching of the bias applied to the detector 5 and the consequent charging and discharging of the detector capacitance $C_d$ whose current primarily flows through the feedback capacitor $C_f$. The output of the synchronous detector 45 is also connected to the input of amplifier 35 through the feedback resistor $R_f$ and to ground through a capacitor 49 so that an analog output signal is developed at the output terminal 51 which is equal to the product of the feedback current $I_f$ and the feedback resistor $R_f$. Large gains following this stage within the overall feedback loop reduce this error voltage to near zero and subsequently maintain the average detector current equal to the reference current.

The electrometer circuit must have very low input bias current (subpicoampere) and be able to keep the input summing node at virtual ground during the detector pulse transient. Pulses of 350 volts with a rise time of 50 nanoseconds are typically applied to the detector, this translates into a slew rate of 7000 volts per microsecond. The detector capacitance, $C_d$, is approximately 1.5 pF. Thus, the slew rate requirement for the electrometer is given by:

$$(S.R.)_e = (7000 V/\mu s) C_d/C_f.$$

The electrometer output must be capable of supplying approximately ten milliamperes charging and discharging current through $C_f$ which is accomplished by cascading a high current buffer amplifier 41 with the output of amplifier 35 which has adequate slew rate but not current drive.

The use of an RC network in the electrometer feedback rather than using only a capacitor limits the low frequency gain of the input stage. This reduces the 1/f noise contribution from the reference current circuit. The electronic input noise of the first stage is dominated by the thermal noise voltage of the feedback resistor and the reference current resistor.

Figure 3:
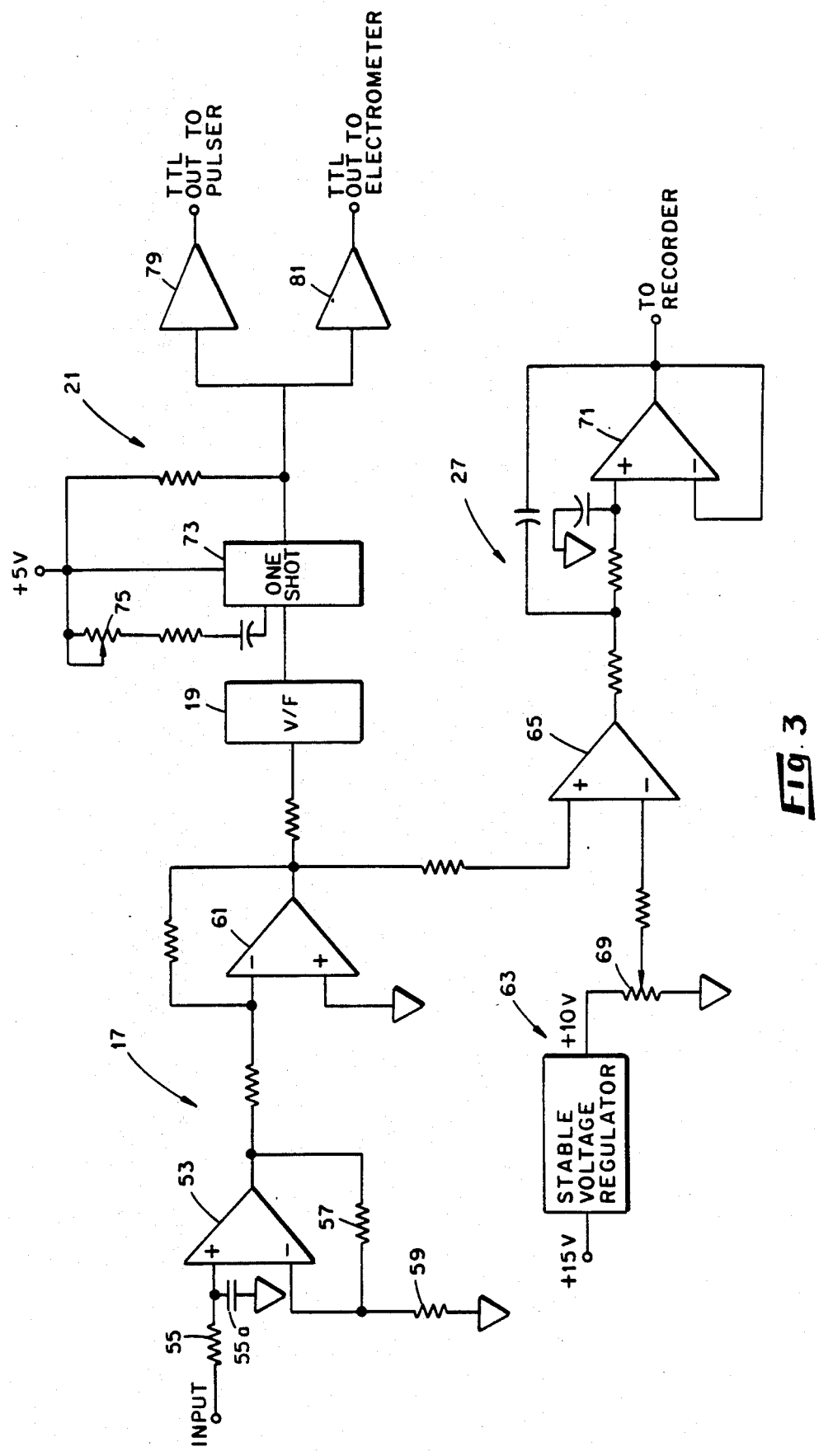
FIG. 3 is a schematic circuit diagram of the interstage gain circuit 17, voltage-to-frequency converter 19, monostable. Multivibrator 21 and instrumentation amplifier 27 shown in block form in FIG. 1.

Thus, an analog output signal is produced at the electrometer output which varies in response to changes in the conductivity or free electron concentration in the detector. Because the output of the electrometer is amplified substantially by the interstage gain circuit 17, variations in the electrometer output voltage are minimized by the closed-loop system and the average detector current remains essentially constant. The gain circuit 17, together with the voltage-to-frequency converter 19, MV 21 and output circuit 37 are shown in FIG. 3. The output of the electrometer 13 is connected to the noninverting input of an operational amplifier 53 through a low pass network consisting of resistor 55 and capacitor 55a. The output of amplifier 53 is connected to the inverting input thereof through a feedback resistor 57. This input terminal is also connected to ground through a resistor 59. The values of resistors 57 and 59 are selected to provide a positive gain of 67. The output of amplifier 53 is connected to the inverting input of a second operational amplifier 61 connected to provide a gain of −10. Thus, the output of amplifier 61 is a signal proportional to the operating frequency.

This signal is used as the chromatographic output signal which is compared with a positive reference voltage from a variable stable reference voltage source 63 by connecting the output of amplifier 61 to the noninverting input of an instrumentation amplifier 65 configured as a gain of unity. The reference voltage source includes a stable voltage regulator 67 having its input connected to a +15V supply and operated to provide a stable 10V output which is connected across a potentiometer 69. The adjustable arm of potentiometer 69 is connected to the inverting input of amplifier 65. The potentiometer is adjusted to offset the output signal produced by the background current level due to the helium carrier gas passing through the HID. The output of the amplifier 65 is connected through a low pass filter amplifier 71 to the recorder 29, as shown in FIG. 1.

As also shown in FIG. 3, the output of amplifier 61 is connected to the input of the voltage-to-frequency converter 19. The circuit 19 is preferrably a model AD650 supplied by Analog Devices, Norwood, Mass. which is configured to produce a 300 kHz pulse frequency for a 10 volt input. The AD650 circuit features a low-noise buried zener reference to generate a switched current source inside the chip. Use of the buried zener reference affords improved low frequency noise performance. The converter 19 triggers a TTL one-shot 73 which forms the adjustable monostable multivibrator 21 shown in FIG. 1. An external timing circuit is provided which includes a potentiometer 75 for varying the period of the one-shot which sets the duration of the high voltage bias pulses applied to the HID 5. The pulses are applied to the pulser 23 and the electrometer 13 through separate TTL buffers 79 and 81, respectively, whose inputs are connected in common to the output of one-shot 73.

Figure 4:
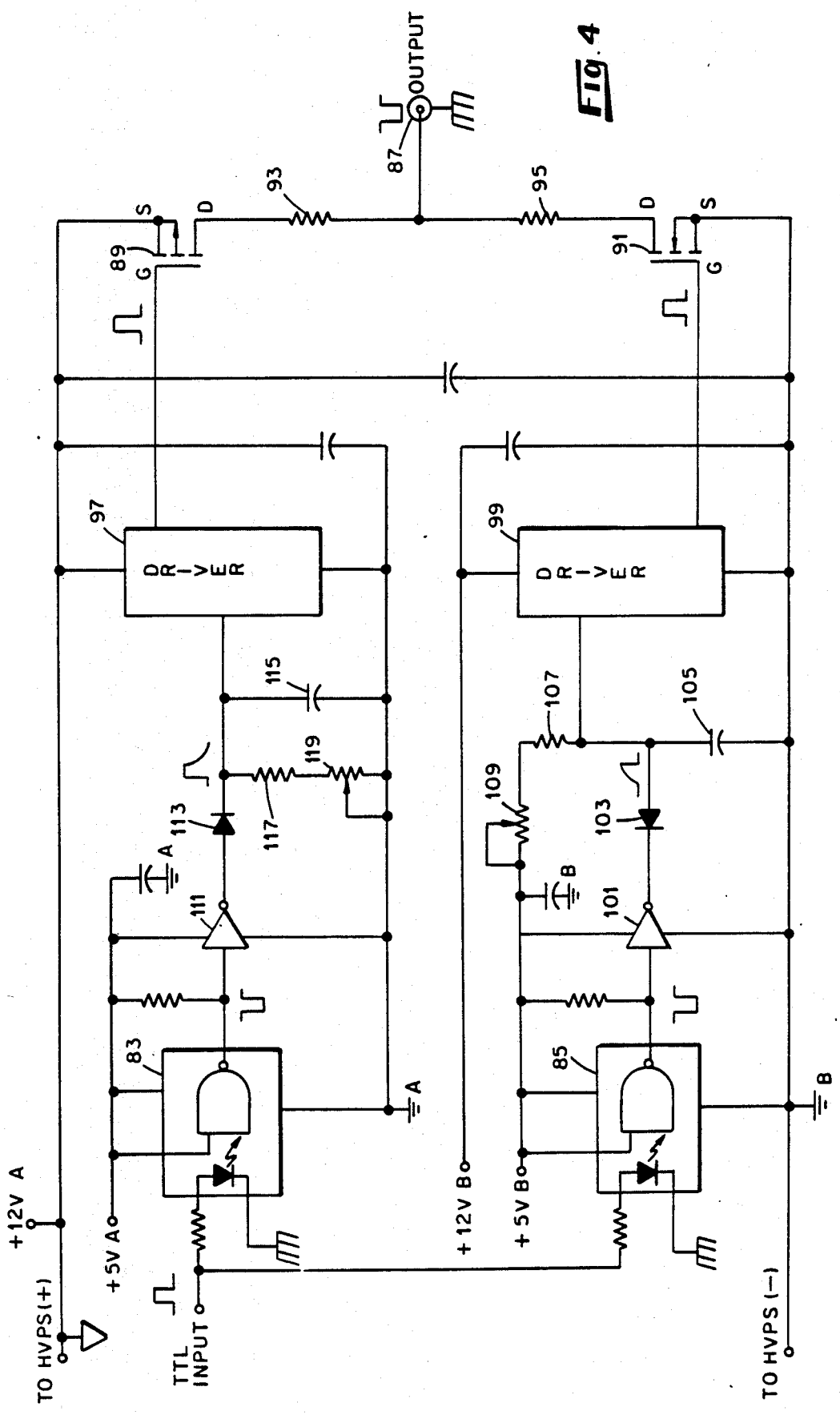
FIG. 4 is a schematic circuit diagram of the high voltage pulser 23 shown in block form in FIG. 1.

The high voltage pulser is shown in FIG. 4. The pulser circuit is capable of switching the high voltage from the high voltage dc power supply 25 of up to 500 volts at a frequency of dc to over 300 kHz at the highest voltage. The frequency and width of the pulses are determined by the input trigger pulses from the TTL buffer 79 of FIG. 3 which are applied to the inputs of separate optoisolator gate input circuits (HP2601) 83 and 85, respectively. These gates form the inputs of separate switching channels to switch the output terminal 87 to either ground or to the selected negative high voltage level at the output of the high voltage power supply (HVPS) 25 in response to the input pulses. The output devices are complementary gate driven MOSFET transistors 89 (MTP2P50) and 91 (MTP2N50) that have 500 V breakdown ratings. The "on" resistance of these devices is quite low, typically 4 ohms each, and they exhibit no charge storage effects typical of bipolar devices to impair switching speed. The negative output pulse rise time of about 50 n sec is dominated primarily by the output resistors 93 and 95 connected respectively between the drain electrodes of transitors 89 and 91 and the output terminal 87 and the connecting cable plus detector 5 capacitances. The output transistors 89 and 91 are driven out of phase, so that only one is on at a time. Since the input gate capacitance of these transistors is large (600–1,000 pF), high current drivers 97 and 99, such as the model D469CJ supplied by Siliconix, Inc., Santa Clara, Calif., are used to drive the output transistors by connecting the outputs thereof to the gates of transistors 89 and 91, respectively. The source electrode of transistor 89 is connected to the positive, or grounded, side of the HVPS 25 while the source electrode of transistor 91 is connected to the negative side of HVPS 25.

The separate switching channels are essentially identical with the exception of different timing circuits to control the switching of transistors 89 and 91 so that transistor 91, which is switched on by the positive going pulse from drive 99 is delayed a short period of time, typically 20 nanoseconds, to insure that transistor 89 is "off" prior to the switching of transistor 91 "on" and vice versa. The separate channels are operated from separate isolated power supplies (A and B), not shown which are referenced to separate local ground terminals A and B, as shown, to provide circuit isolation from the HVPS 25. Thus, the output of the optoisolator gate 85 responds to the positive pulse applied to the input from the monostable 21, FIG. 1, to produce a negative output pulse which is applied to an inverter 101 whose output is connected to the input of current driver 99 through a diode 103 having its cathode electrode connected to the output of inverter 101. The anode of diode 103 is connected to ground terminal B through a capacitor 105 and to a +5V terminal of the B power supply through resistors 107 and 109 respectively forming the timing circuit for this switching channel. During the period that the input pulse to gate 85 is low, diode 103 conducts due to the output of inverter 101 being low, holding the input to drives 99 low. Thus, when the output of inverter 101 goes high, in response to the input pulse going high, diode 103 is reverse biased causing capacitor 105 to be charged to the +5VB voltage level at a rate determined by the time constant of the timing circuit producing the pulse shape shown at the input of driver 99, thereby delaying the activation of driver 99 and thus the switching of transistor 91 to the conducting state by applying a positive going pulse to the gate thereof.

Similarly the output of gate 83 of the switching channel for transistor 89 is connected to the input of an inverter 111 whose output is connected through a diode 113 to the input of current driver 97 with the anode of diode 113 connected to the output of inverter 111. The cathode of diode 113 is connected to ground terminal A through an RC timing circuit found of a capacitor 115 in parallel with series connected resistors 117 and 119. In this case diode 113 is reverse biased during the off portion of the input switching pulse which forces the output of inverter 111 low and output transistor 89 is turned "on" switching the output terminal 87 to ground potential. When the input pulse goes high the output of inverter 111 also goes high causing diode 113 to conduct, thereby activating the current driver 97 to immediately turn transistor 89 off. When the input pulse returns to the low state diode 113 is again reverse biased and the capacitor 115, which is charged during the conducting period of diode 113, is discharged through resistors 117 and 119 at a rate determined by the RC timing constant to produce the desired trailing edge pulse shape applied to driver 97, thereby delaying the return of output transistor 89 to the on state. Thus, the switching of transistor 89 to the on condition is delayed sufficiently to allow transistor 91 to be turned off following the application of each input pulse from the monostable multivibrator 21, FIG. 1. Thus, it will be seen that high voltage pulses are applied to the HID 5 at the feedback frequency determined by the amplitude of the signal applied to the input of the voltage-to-frequency converter 19, FIG. 1, having a period equal to the period of the monostable multivibrator 21. This pulse period is usually set to provide an approximate 80% duty cycle for the pulses applied to the HID.

Figure 5:
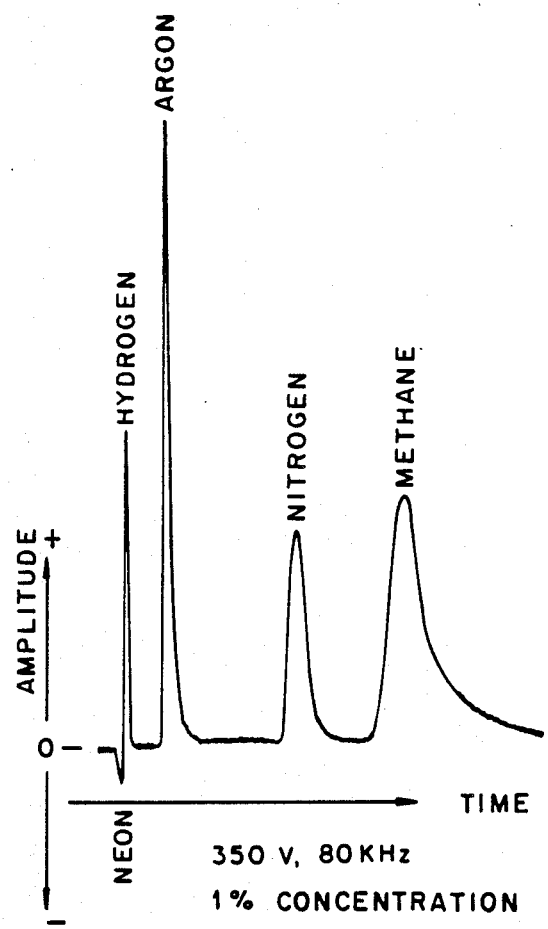
FIG. 5 is a graph of the system output response for a 1% concentration mixture of neon, hydrogen, argon, nitrogen and methane with ultra-high purity helium as the carrier gas with an initial setting of 350 volts and 80 kHz.
Figure 6:
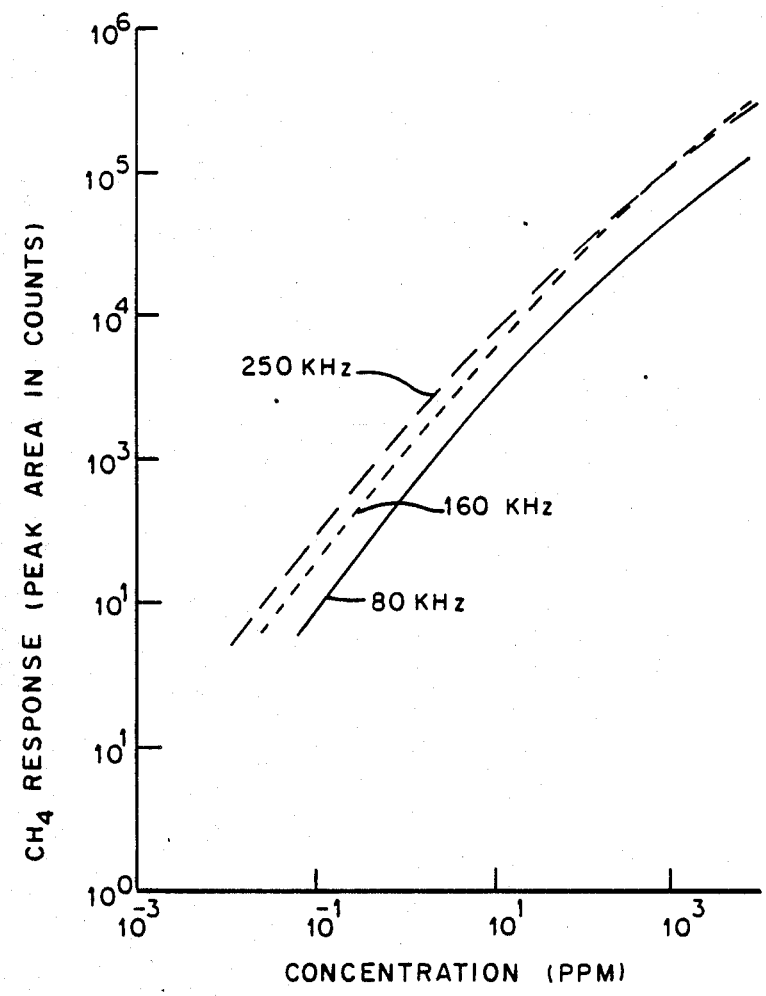
FIG. 6 is a set of 3 calibration curves obtained for methane at baseline frequency settings of 250, 160, and 80 kHz, respectively.

The HID is a sensitive device for gas chromatographic detection. It is primarily used to determine volatilizable compounds that are difficult to determine with other available detector systems (e.g., low concentrations of the permanant gases). Operation of the HID in a constant-current, variable-frequency mode improves the detector's stability, preventing spontaneous breakdown when high concentrations of an analyte are introduced into the detector, reduces background current levels, and increases the dynamic range. Calibration curves for the closed-loop system were obtained by analyzing standard gas mixtures which were generated by diluting a 1% concentration mixture of neon, hydrogen, argon, nitrogen, and methane (balance high purity helium) with ultra-high purity helium. The analyses were performed at 80, 160, and 250 kHz at a fixed pulse width of 2.4 usec and at 350 V. Separations were carried out at room temperature on a 1.8 m×2.1 mm I.D., 3.2 mm O.D. stainless steel column packed with molecular sieve 5 A (80–100 mesh) using ultra-high purity helium as the carrier gas at a flow rate of 35 ml/min. Concentrations from 1% to approximately 100 parts per billion (ppb) could be analyzed. This contrasts to DC operation where the maximum concentration which can be analyzed is approximately 100 parts per million (ppm). Above 100 ppm in a DC mode the peaks for neon, hydrogen, argon, oxygen, and nitrogen become deformed (W-shaped) and cannot be quantitated. Furthermore, above 1000 ppm the detector cell breaks down, delaying additional analyses until baseline conditions are reestablished. FIG. 5 shows a chromatogram for a 1% concentration of the gases obtained with the detector pulsed at 80 kHz. Calibration curves for methane at 250, 160, and 80 kHZ covering 6 to 7 orders of magnitude are presented in FIG. 6.

Depending upon the analytical requirements the operating frequency range and pulse duty cycle may be adjusted to cover a broad detecting range. As an analyte passes through the detector the system automatically decreases the operating frequency to compensate for the increase in ionization current to maintain an average detector current substantially equal to the reference current supplied to the input of the electrometer, as shown in FIG. 1. High concentrations of an analyte are best analyzed at low frequencies and duty cycles while the greatest sensitivity for low concentrations is obtained at high frequencies and duty cycles.

The closed-loop control system allows stable operation of the detector at high voltages. Thus, it will be seen that an improved helium ionization detection system has been provided which is brought about by an improved operating system in which the detector is combined with an electronic feedback loop that pulses the detector bias voltage at a frequency to maintain constant average current through the detector.

We claim:

1. In combination, a helium ionization detector and a closed-loop control system for pulsed operation of the helium ionization detector, comprising:

a helium ionization detector having an anode and a cathode electrodes between which a helium carrier gas containing an ionizable component whose concentration is to be detected is introduced to be ionized to produce an ionization current therein which flows through said electrodes when a high voltage bias is applied between said electrodes;

a high voltage pulser means for generating and applying selected amplitude high voltage bias pulses between said electrodes of said detector in response to input switching pulses applied to an input thereof;

a reference current generator means for generating a selected reference current corresponding to a desired average ionization current in said detector;

an electrometer circuit means for generating an output signal at an output terminal thereof that varies in inverse proportion to the change in ionization current in said detector which in turn varies in proportion to the concentration of said ionizable component within said detector, said electrometer circuit means including an input current summing junction connected to receive said reference current and said ionization current, an electrometer amplifier means having an input connected to said summing junction to receive a current signal equal to the difference between said reference current and said ionization current for generating an output signal having an amplitude which varies in inverse proportion to the change in ionization current in said detector, and a synchronous detector means connected to the output of said electrometer amplifier means and operable in response to a trigger pulse applied to an enabling input thereof for applying the output of said electrometer amplifier means to said output terminal of said electrometer circuit means for the period said trigger pulse is applied to said enabling input of said synchronous detector means;

a switching pulse generating means responsive to said output signal of said electrometer circuit means for generating and applying said switching pulses to said high voltage pulser means at a frequency and a selected duty cycle which maintains a constant average ionization current flowing in said detector which is substantially equal to said reference current as the concentration of said ionizable component varies and generating and applying said trigger pulse to said enabling input of said synchrounous detector means during the period between each of said high voltage pulser means so that only the dc component of said output signal of said electrometer amplifier means is applied to the output terminal of said electrometer circuit means; and means for sensing the amplitude of the output of said electrometer circuit means as an indication of the concentration of said ionizable component being detected by said helium ionization detector.

2. The combination set forth in claim 1 further including a high gain amplifier connected in series with said output terminal of said electrometer circuit means and wherein said electrometer circuit means includes a first amplifier having an inverting input connected to said summing junction, a non-inverting input connected to ground potential and an output, a second amplifier having an input connected to the output of said first amplifier and an output connected to said synchronous detector means, a feedback network including a first resistor connected between the output of said second amplifier and said output terminal of said electrometer circuit means, a second resistor ($R_f$) connected between said output terminal and said inverting input of said first amplifier and a first capacitor ($C_r$) connected between the output of said second amplifier and said inverting input of said first amplifier, and a second capacitor connected between said output terminal of said electrometer circuit means and ground potential so that a signal is developed at said output terminal of said electrometer circuit means when said synchronous detector means is enabled which has an amplitude equal to the product of a feedback current $I_f$ flowing through said resistor $R_f$ and the resistance of said feedback resistor $R_f$, where $I_f$ is equal to the difference between said ionization current and said reference current.

3. The combination as set/forth in claim 2 wherein said high voltage pulser means includes a variable high voltage dc power source having a selectable output voltage range up to about 500 volts, a high voltage switching means operable in response to said switching pulses and the output voltage of said dc power source for generating said high voltage bias pulses at an output thereof having an amplitude corresponding to a selected output voltage of said said power supply and a frequency and pulse width corresponding to the width of said switching pulses.

4. The combination as set forth in claim 2 wherein said high voltage switching means includes first and second complementary MOSFET transistors connected in series opposition between the output of said high voltage power supply and ground potential so that the common connecting point of said first and second MOSFET transistors forms the output of said high voltage pulser means and first and second gate drive channels connected to the gate electrodes of said first and second MOSFET transistors, respectively, and each of said first and second gate drive channels responsive to said switching pulses to generate gate drive signals to the gates of said first and second MOSFET transistors so that said output of said high voltage pulser means is alternatively switched between the output of said high voltage power source and ground potential at a frequency corresponding to the frequency of said switching pulses.

5. The combination as set forth in claim 4 wherein said switching pulse generating means includes a voltage-to-frequency converter means connected to the output of said high gain amplifier for generating a signal at an output thereof having a frequency proportional to the amplitude of the output of said high gain amplifier means and a variable period monostable multivibrator connected to the output of said voltage-to-frequency converter means so that said switching pulses are generated at an output of said monostable multivibrator having a selected period and a frequency corresponding to the frequency of said signal from said voltage-to-frequency converter means.

6. The combination as set forth in claim 4 wherein the amplitude of said output signal of said electrometer circuit means is substantially proportional to the difference between said reference current and said ionization current and applied to said voltage-to-frequency converter means so that the frequency of said switching pulses are decreased as the concentration of said component to be detected by said detector increases, so as to maintain a substantially constant average detector ionization current.

* * * * *